US00PP30929P2

(12) United States Plant Patent
Danziger

(10) Patent No.: US PP30,929 P2
(45) Date of Patent: Oct. 8, 2019

(54) ***PETUNIA* PLANT NAMED 'DPECAPNKLC'**

(50) Latin Name: ***Petunia* hybrid**
Varietal Denomination: DPECAPNKLC

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/350,025

(22) Filed: Sep. 13, 2018

(51) Int. Cl.
*A01H 5/02* (2018.01)
*A01H 6/82* (2018.01)

(52) U.S. Cl.
USPC ..... Plt./356.17
CPC ..... *A01H 6/82* (2018.05); *A01H 5/02* (2013.01)

(58) Field of Classification Search
USPC ..... Plt./356.1, 356.17, 356.13
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Petunia* cultivar named 'DPECAPNKLC' is disclosed, characterized by a mounded, compact growth habit, and large, light pink flowers with a dark violet throat and purple veins. The plants are very well branched with a medium-low vigor. The new variety is a *Petunia*, normally produced as an outdoor garden or container plant.

2 Drawing Sheets

Figure 1:
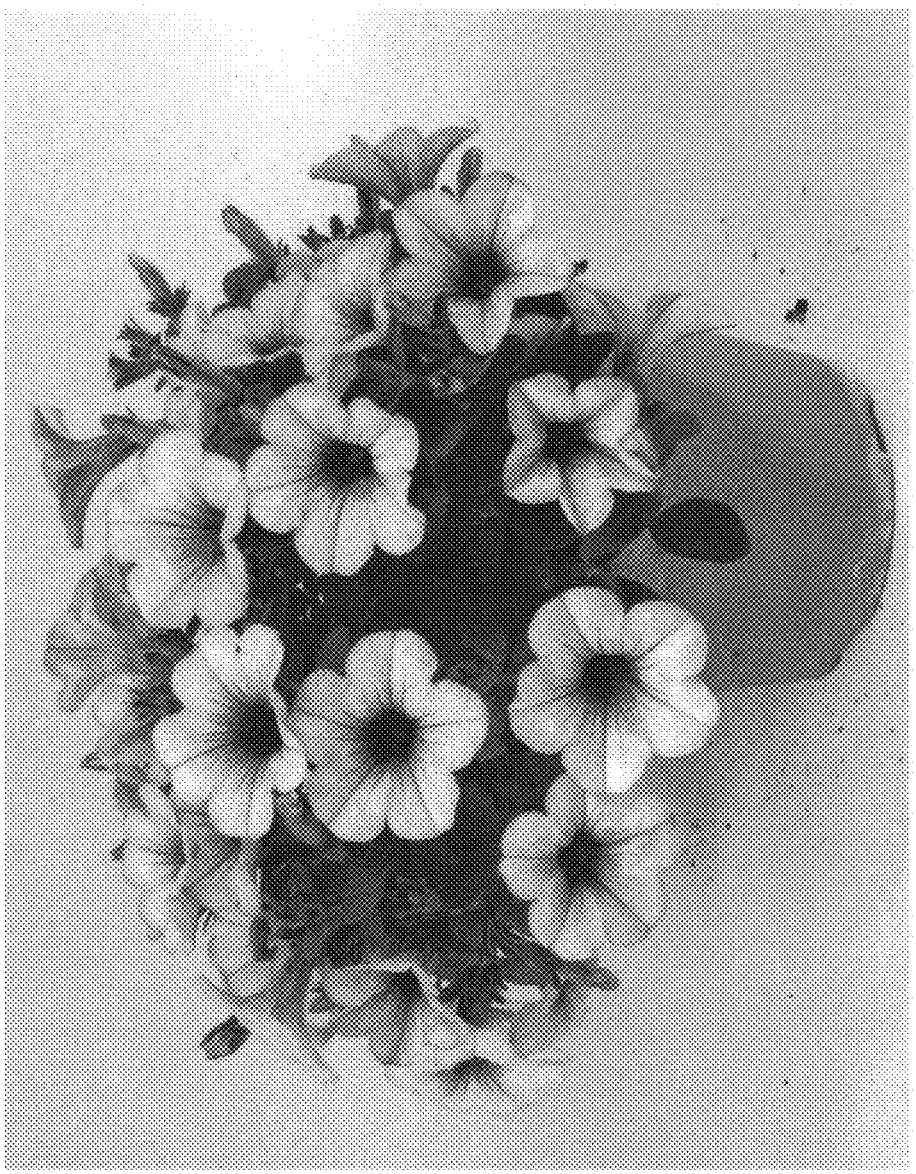

Latin name of the genus and species: *Petunia* hybrid.
Variety denomination: 'DPECAPNKLC'.

BACKGROUND OF THE INVENTION

The new *Petunia* hybrid cultivar is a product of a planned breeding program conducted by the inventor, Gavriel Danziger in Moshav Mishmar Hashiva, Israel. The objective of the breeding program was to produce new *Petunia* varieties with interesting flower color patterns. The cross resulting in this new variety was made during August of 2013.

The seed parent is the unpatented, propriety variety referred to as *Petunia* 'cv. 13-7416'. The pollen parent is the unpatented, propriety variety referred to as *Petunia* 'cv. 13-7452'. The new variety was discovered in May of 2014 by the inventor in a group of seedlings resulting from the 2013 crossing, in a greenhouse in Moshav Mishmar Hashiva, Israel.

Asexual reproduction of the new cultivar 'DPECAPNKLC' was first performed by terminal vegetative cuttings during May of 2014, at a greenhouse in Moshav Mishmar Hashiva, Israel. Subsequent asexual propagation has shown that the unique features of this cultivar are stable and reproduced true to type in more than 25 successive generations. 'DPECAPNKLC' was first made available to the public Oct. 1, 2017 in Taiwan. This was a sale by the inventor or one who obtained the claimed invention directly or indirectly from the inventor. This public disclosure falls within the exception allowed under 102(b)(1).

SUMMARY OF THE INVENTION

The cultivar 'DPECAPNKLC' has not been observed under all possible environmental conditions. The phenotype may vary somewhat with variations in environment such as temperature, day length, and light intensity, without, however, any variance in genotype.

SUMMARY OF THE INVENTION

The cultivar 'DPECAPNKLC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPECAPNKLC' These characteristics in combination distinguish 'DPECAPNKLC' as a new and distinct *Petunia* cultivar:

1. Mounded, compact growth habit.
2. Very well branched plant with medium-low vigor.
3. Flowers color is light pink with a dark violet throat and purple veins.
4. Flower size is large.
5. Abundant flowering.

PARENT COMPARISON

Plants of the new cultivar 'DPECAPNKLC' are similar to plants of the seed parent, *Petunia* 'cv. 13-7416' in most horticultural characteristics, however, plants of the new cultivar 'DPECAPNKLC' differ in the following;

1. 'Cv. 13-7416' has a semi-trailing growth habit, while 'DPECAPNKLC' has a mounded and compact growth habit.
2. 'Cv. 13-7416' is a well branched plant with low vigor while 'DPECAPNKLC' is a very well branched plant with medium-low vigor.
3. 'Cv. 13-7416' flower color is light violet with purple veins, while 'DPECAPNKLC' flower color is light pink with a dark violet throat and purple veins.
4. 'Cv. 13-7416' flower size is medium while 'DPECAPNKLC' flower size is large.
5. 'Cv. 13-7416' has medium quantity of flowering while 'DPECAPNKLC' has abundant flowering.

Plants of the new cultivar 'DPECAPNKLC' are similar to plants of the pollen parent in most horticultural characteristics however, plants of the new cultivar 'DPECAPNKLC' differ in the following;

1. 'Cv. 13-7452' has a semi trailing growth habit while 'DPECAPNKLC' has mounded and compact growth habit.
2. 'Cv. 13-7452' is a medium-branching plant with medium vigor while 'DPECAPNKLC' is a very well branched plant with medium-low vigor.
3. 'Cv. 13-7452' flower color is pink with dark pink veins while 'DPECAPNKLC' flower color is light pink with a dark violet throat and purple veins.
4. 'Cv. 13-7452' flower size is medium-small while 'DPECAPNKLC' flower size is large.
5. 'Cv. 13-745'2 has low quantity of flowering while 'DPECAPNKLC' has abundant flowering.

COMMERCIAL COMPARISON

Plants of the new cultivar 'DPECAPNKLC' can be compared to the commercial variety *Petunia* 'DPECAPBURG', U.S. Plant Pat. No. 29,340. These varieties are similar in most horticultural characteristics; however, 'DPECAPNKLC' differs in the following:

1. Growth habit of 'DPECAPBURG' is semi trailing, while 'DPECAPNKLC' has mounded growth habit.
2. Flower color of 'DPECAPBURG' is purple with blue throat, while 'DPECAPNKLC' has light pink flowers with dark violet throat and purple veins.
3. 'DPECAPBURG' is more vigorous than 'DPECAPNKLC'.

Plants of the new cultivar 'DPECAPNKLC' can also be compared to the unpatented commercial variety *Petunia* 'DANRAY2'. These varieties are similar in most horticultural characteristics; however, 'DPECAPNKLC' differs in the following:

1. Flower size of 'DANRAY2' is extra-large, while the flower size of 'DPECAPNKLC' is large.
2. Flower color of 'DANRAY2' is dark pink with a white throat, while 'DPECAPNKLC' has light pink flowers with dark violet throat and purple veins.
3. 'DANRAY2' is more vigorous than 'DPECAPNKLC'.

BRIEF DESCRIPTION OF THE PHOTOGRAPHS

The accompanying photograph in FIG. 1 illustrates in full color a typical plant of 'DPECAPNKLC' grown in a greenhouse, in Moshav Mishmar Hashiva, Israel.

Figure 2:
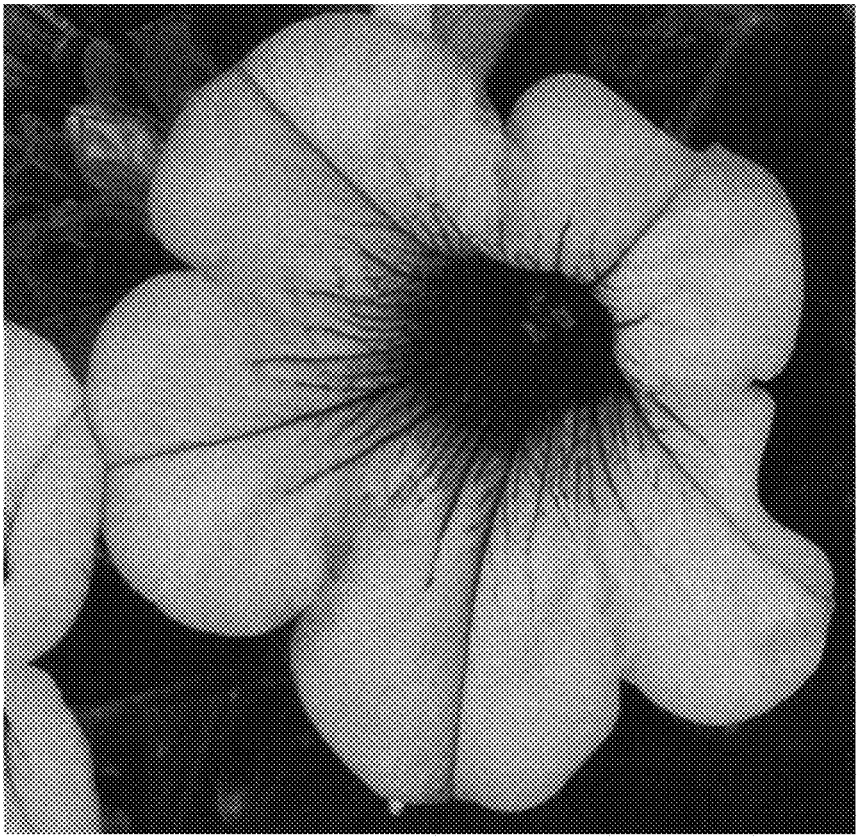

FIG. 2 illustrates in full color a typical mature flower of 'DPECAPNKLC' during Spring. Age of the plant photographed is approximately 60 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPECAPNKLC' plants grown in greenhouse in Moshav Mishmar Hashiva, Israel, under natural lighting. Measurements were taken during April of 2015. The plants were approximately 60 days from a rooted cutting in a 13 cm pot. The growing temperature ranged from 20° C. to 35° C. during the days, 17° C. to 23° C. during the nights. Measurements and numerical values represent averages of typical plant types.

Botanical classification: *Petunia* hybrid 'DPECAPNKLC'.

PROPAGATION

Time to initiate roots: 10 to 14 days at approximately 20° C.

Root description: Fibrous. Tan, not accurately measured with a color chart.

PLANT

Growth habit: Mounded.

Pot size of plant described: 13 cm.

Height: To top of flowers: about 20 cm.

Plant spread: About 50 cm.

Growth rate: Medium.

Branching characteristics:

Length of primary lateral branches: About 25 cm.

Diameter of lateral branches: About 0.2 cm.

Quantity of primary lateral branches: 8.

Characteristics of primary lateral branches:

*Form*.—Cylindrical.

*Diameter*.—About 0.2 cm.

*Color*.—RHS Yellow-Green 146 B.

*Texture*.—Pubescent.

*Strength*.—Good.

Internode length: About 1.5 cm.

FOLIAGE

Leaf:

*Arrangement*.—Opposite.

*Quantity*.—Approximately 30 per branch.

*Average length*.—4.5 cm.

*Average width*.—2 cm.

*Shape of blade*.—Elliptic.

*Apex*.—Acute.

*Base*.—Acute.

*Margin*.—Entire.

*Texture of top surface*.—Velvety.

*Texture of bottom surface*.—Velvety.

*Pubescence*.—Soft, short upper and lower surfaces.

*Aspect*.—90 degrees angle of attachment. Mainly flat, slight upward curve.

*Color*.—Young foliage upper side: RHS Yellow-Green 146 A. Young foliage under side: RHS Yellow-Green 146 B. Mature foliage upper side: RHS Yellow-Green 146 A. Mature foliage under side: RHS Yellow-Green 146 B.

*Venation*.—Type: Pinnate. Venation color upper side: RHS Yellow-Green 146 B. Venation color under side: RHS Yellow-Green 146 C.

*Petiole*.—Length: About 0.5 cm. Diameter: About 0.2 cm. Color: RHS Yellow-Green 146 C. Texture: Velvety.

FLOWER

Natural flowering season: Spring, Summer and Autumn.

Days to flowering from rooted cutting: About 30 days.

Inflorescence and flower type and habit: Axillary, single flower, Salverform shape, erect habit.

Rate of flower opening: 2 to 3 days from bud to fully opened flower.

Flower longevity on plant: 3-6 days.

Approximate quantity of flowers per plant: About 70.
Persistent or self-cleaning: Self-cleaning.
Bud:
*Shape*.—Tubular.
*Length*.—About 4 cm.
*Diameter*.—About 0.7 cm.
*Color*.—RHS Purple-Violet N 80 C.
Flower size:
*Diameter*.—About 5.5 cm.
*Flower tube length*.—About 3 cm.
*Flower tube diameter at distal end*.—About 1.1 cm.
*Flower tube diameter at proximal end*.—About 0.2 cm.
Petals:
*Length from throat*.—About 2 cm.
*Width*.—About 2.2 cm.
*Quantity*.—5.
*Texture*.—Velvety.
*Apex*.—Blunt.
*Margin*.—Entire.
Color:
When opening:
*Upper surface*.—RHS Purple 75 A.
*Lower surface*.—RHS Purple 76 B.
Fully opened:
*Upper surface*.—RHS Purple 75 B.
*Lower surface*.—RHS Purple 76 B.
*Flower throat* (*inside*).—RHS Violet-Blue 90 B.
*Flower throat, vein*.—RHS Red-Purple 72 B.
*Flower tube* (*outside*).—RHS Violet N 87 B.
*Flower tube, vein*.—RHS Yellow-Green 146 C.
Fading:
*Petals fading to*.—RHS Purple 76 C.
Calyx/sepals :
*Quantity per flower*.—5.
*Shape*.—Linear.
*Length*.—About 1.5 cm.
*Width*.—About 0.2 cm.
*Apex*.—Acute.
*Base*.—Cuneate.
*Margin*.—Entire.
*Texture*.—Velvety.
*Color*.—Upper Surface: RHS Yellow-Green 146 A. Lower Surface: RHS Yellow-Green 146 B.
Peduncle: Not present.
Pedicel:
*Length*.—About 2 cm.
*Diameter*.—About 0.1 cm.
*Color*.—RHS Yellow-Green 146 C.
*Orientation*.—45 degrees.
Fragrance: None.

REPRODUCTIVE ORGANS

Stamens:
*Number*.—5.
*Filament length*.—About 2 cm.
Anthers:
*Length*.—About 0.2 cm.
*Shape*.—Rounded.
*Color*.—RHS Violet-Blue 95 D.
*Pollen*.—Color: RHS Violet-Blue 98D. Quantity: Plenty.
Pistil:
*Number*.—1.
*Length*.—About 2.4 cm.
*Style*.—Length: About 2.0 cm. Color: RHS Yellow-Green 149 C.
*Stigma*.—Shape: Rounded. Color: RHS Purple-Violet N82C. Ovary Color: RHS Yellow-Green 144B.

OTHER CHARACTERISTICS

Seeds and fruits: About 60 Brown (near RHS Brown 200C), rounded seeds of about 0.5 mm diameter, per one brown, conical capsule.
Disease/pest resistance: Neither resistance nor susceptibility to the normal diseases and pests of *Petunia* have been observed. Typical well-known diseases include: *Botrytis cineria, Fusarium, Pythium, Phytophthora,* and *Rhizoctonia* species. Typical well-known pests include: Leaf miners, spider mites, thrips and possibly caterpillars.
Temperature tolerance: 5-40° C.

What is claimed is:

1. A new and distinct cultivar of *Petunia* plant named 'DPECAPNKLC' as herein illustrated and described.

* * * * *